US011228235B2

(12) United States Patent
Cestero et al.

(10) Patent No.: US 11,228,235 B2
(45) Date of Patent: Jan. 18, 2022

(54) ADJUSTABLE LOCKING SURGICAL RETRACTOR

(71) Applicants: Ramon F. Cestero, San Antonio, TX (US); Justin Alexander Long, San Antonio, TX (US)

(72) Inventors: Ramon F. Cestero, San Antonio, TX (US); Justin Alexander Long, San Antonio, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 751 days.

(21) Appl. No.: 15/751,694

(22) PCT Filed: Aug. 10, 2016

(86) PCT No.: PCT/US2016/046432
§ 371 (c)(1),
(2) Date: Feb. 9, 2018

(87) PCT Pub. No.: WO2013/009968
PCT Pub. Date: Jan. 17, 2013

(65) Prior Publication Data
US 2018/0234009 A1 Aug. 16, 2018

Related U.S. Application Data

(60) Provisional application No. 62/203,269, filed on Aug. 10, 2015.

(51) Int. Cl.
*A61B 90/50* (2016.01)
*A61B 17/02* (2006.01)
(Continued)

(52) U.S. Cl.
CPC ............ *H02M 1/32* (2013.01); *A61B 17/0206* (2013.01); *A61B 17/0293* (2013.01);
(Continued)

(58) Field of Classification Search
CPC . A61B 17/0206; A61B 17/0293; A61B 17/02; A61B 17/0218; A61B 17/025;
(Continued)

(56) References Cited

U.S. PATENT DOCUMENTS 1,919,120 A 7/1933 O'Connor et al.
1,963,173 A * 6/1934 Morin ................ A61B 17/0293
600/233

(Continued)

FOREIGN PATENT DOCUMENTS

CN 201939399 8/2011
CN 203815511 9/2014
(Continued)

OTHER PUBLICATIONS

Office Action and Search Report Issued in Corresponding Chinese Patent Application No. 2016800469810, dated Oct. 22, 2019. English Translation.
(Continued)

*Primary Examiner* — Marcela I. Shirsat

(57) ABSTRACT

A surgical retractor assembly for providing surgical exposure. The surgical retractor assembly consists of multiple ring segments connected by adjustable ratchet mechanisms to form a complete ring. The ratchet mechanisms are attached to tissue retractor blades which provide exposure of the wound when expanded, without the requirement of a direct connection/attachment to an operating table. The tissue retractor blades are attached in a manner which is adjustable and facilitates the ability of the overall surgical retractor assembly (ring segments and connectors) to be
(Continued)

raised or lowered with respect to the patient. The ring segments also allow attachments of additional retractor blades or other surgical retractor accessories for additional surgical exposure.

42 Claims, 16 Drawing Sheets

(51) Int. Cl.
| | | |
|---|---|---|
| *A61B 17/34* | (2006.01) | |
| *A61B 1/32* | (2006.01) | |
| *A61B 17/00* | (2006.01) | |
| *H02M 1/32* | (2007.01) | |
| *B60R 16/033* | (2006.01) | |
| *H03K 17/08* | (2006.01) | |
| *H02M 1/44* | (2007.01) | |
| *H02M 3/04* | (2006.01) | |

(52) U.S. Cl.
CPC ............ *A61B 90/50* (2016.02); *B60R 16/033* (2013.01); *H03K 17/08* (2013.01); *A61B 1/32* (2013.01); *A61B 17/0218* (2013.01); *A61B 17/3439* (2013.01); *A61B 17/3462* (2013.01); *A61B 2017/00407* (2013.01); *H02M 1/44* (2013.01); *H02M 3/04* (2013.01)

(58) Field of Classification Search
CPC ............ A61B 17/3423; A61B 17/3421; A61B 17/3462; A61B 17/3439; A61B 2017/0206; A61B 2017/0293; A61B 2017/0225; A61B 2017/0287; A61B 2017/0256; A61B 2017/3445; A61B 2017/0237; A61B 2017/00407; A61B 90/50; A61B 1/32; F16B 7/04; F16B 7/042
USPC ....... 600/233, 231, 201, 208, 210, 211, 235, 600/215, 213, 216, 219, 221, 222
See application file for complete search history.

(56) References Cited

U.S. PATENT DOCUMENTS

| | | | | |
|---|---|---|---|---|
| 2,751,902 | A | | 6/1956 | Loeffler |
| 5,231,974 | A | * | 8/1993 | Giglio ................ A61B 17/0293 600/206 |
| 5,299,563 | A | * | 4/1994 | Seton ................ A61B 17/0293 128/898 |
| 8,900,137 | B1 | | 12/2014 | Lovell et al. |
| 2002/0183833 | A1 | | 12/2002 | Stevens et al. |
| 2003/0065251 | A1 | * | 4/2003 | Feng ................ A61B 17/0293 600/229 |
| 2009/0287062 | A1 | | 11/2009 | Farley |
| 2010/0280586 | A1 | | 11/2010 | Case et al. |
| 2011/0201897 | A1 | * | 8/2011 | Bertagnoli ......... A61B 17/0206 600/229 |
| 2012/0296170 | A1 | | 11/2012 | Wilkins et al. |
| 2013/0158359 | A1 | | 6/2013 | Predick et al. |
| 2014/0114137 | A1 | * | 4/2014 | Reglos ............... A61B 17/3421 600/219 |

FOREIGN PATENT DOCUMENTS

| | | |
|---|---|---|
| DE | 202014003736 | 5/2014 |
| JP | H04-4500014 | 1/1992 |
| JP | H10-033543 | 2/1998 |
| WO | WO 01/80725 | 11/2001 |
| WO | WO 2010/100592 | 9/2010 |

OTHER PUBLICATIONS

Extended European Search Report Issued in European Application No. 16835867.9, dated Mar. 11, 2019.
International Preliminary Report on Patentability issued in Application No. PCT/US2016/046432, dated Feb. 22, 2018.
International Search Report and Written Opinion issued in Application No. PCT/US2016/046432, dated Dec. 26, 2016.
Office Action Issued in Corresponding Japanese Patent Application No. 2018527842, dated Aug. 26, 2020.

* cited by examiner

ADJUSTABLE LOCKING SURGICAL RETRACTOR

This application is a national phase application under 35 U.S.C. § 371 of International Application No. PCT/US2016/046432, filed Aug. 10, 2016, which claims priority to U.S. Provisional Patent Application Ser. No. 62/203,269 filed Aug. 10, 2015, each of which is incorporated herein by reference in its entirety.

BACKGROUND

Abdominal operations in both emergency and elective surgery settings require adequate exposure of abdominal contents in order for the surgeon to properly visualize areas of injury or disease. This is typically accomplished by the use of static metal retractors. Two of the most common retractor mechanisms in current use are the Balfour retractor and the Bookwalter retractor. Each of these retractors presents advantages and disadvantages in their design and use. The Balfour retractor consists of a frame with integrated metal blades on a ratchet system which, when engaged, retracts the abdominal wall laterally, thereby exposing the abdominal contents and allowing the surgeon to operate. The Bookwalter mechanism consists of a supporting frame attached to the operating table upon which a rigid non-adjustable metal ring is attached to which retractor blades are then attached individually. Despite the ubiquitous use of these retractors, these surgical retractor mechanisms have not been improved upon for considerable time.

The Balfour retractor is perhaps the most commonly utilized abdominal retractor due its simple design, ease of use, and rapid exposure of the abdomen, particularly in trauma and emergency surgery settings when time is of the essence. Since it does not require the attachment of a metal frame to the operating room bed, as with the Bookwalter retractor, valuable time is not wasted and it can be quickly inserted after the abdominal incision is created.

Despite the Balfour retractor's prevalence in operating rooms and ease of utilization, there are several limitations to its use. It provides inadequate abdominal exposure of large or obese patients. In larger or obese patients, the current design of the standard Balfour retractor often does not provide enough retraction to adequately expose the abdomen. The frame along which the retractor blades run is typically too short for larger or obese patients, resulting in suboptimal exposure and frequently necessitating conversion to another retractor system. Due to the Balfour retractor's inherently limited design, the surgical incision is only retracted along one axis (transverse), limiting overall exposure of the wound. An optional additional retractor blade (bladder blade) can be attached which only adds retraction in the inferior direction, typically resulting in suboptimal exposure requiring conversion to another retractor system.

The standard Balfour retractor does not provide an additional frame upon which to attach additional retractor blades except for a single bladder blade. This significantly limits the ability to retract additional incisional or abdominal contents compared to other retractor mechanisms, thereby limiting surgical exposure. Additionally, the Balfour retractor system commonly poses a significant problem during its use due to the unintentional movement and migration of the retractor blades along the edges of the surgical wound. The two retractor blades which provide lateral traction on the wound edges (or abdominal wall in abdominal operations) frequently unintentionally migrate to either the superior or inferior parts of the wound, causing rotation of the entire retractor mechanism, loss of wound edge retraction, and requiring either time-consuming repositioning of the retractor or conversion to another type of retractor system. This is particularly common in large or obese patients.

The Bookwalter retractor is typically the retractor system used when the Balfour retractor system is considered inadequate or ineffective. It consists of a supporting metal rod which is attached to a side rail on the operating room table by a non-sterile individual in the operating room after the patient is under anesthesia (the rail on the operating table is not considered part of the sterile operating field). A second metal arm is then attached to this supporting rod, and a rigid circular or oblong metal ring is then attached to the second metal arm. Once this is in place, individual retractor blades can then be attached, using the rigid ring for support.

Despite the popularity of the Bookwalter retractor it also presents several limitations. The Bookwalter retractor mechanism involves fixation to the operating room table which requires attachment by a non-sterile individual in the operating room. Occasionally this causes concerns in maintenance of the sterile field, as the surgeon may need to place his hands below the sterile barrier in order to assist and properly place the retractor arm. In addition, the multiple arms which require setup before surgical retraction is achieved mandates a significant amount of time in instrument setup, rendering this system inadequate for emergency settings or operations when time is of the essence. The circumferential ring used in the Bookwalter system is not expandable and frequently limits the placement of additional retractors in both the longitudinal and transverse axes. In addition, the fixed sizes of the rings do not allow adjustment of retraction depending on the individual physical characteristics of each patient and various types and sizes of wounds or incisions. The Bookwalter system also requires frequent repositioning by the surgical team during its use. After the Bookwalter system is set up and attached to the bed frame, the ring system is thereby fixed in place and additional retractors are attached. However, as the operation progresses and surgical exposure requirements change, the system needs to be repositioned to place the static non-expandable ring into the correct location. This requires interruption of the operation, removal of the retractor blades, repositioning of the ring, and reattachment of the retractor blades, again requiring significant time. There is an existing need for additional retractor systems.

SUMMARY

Certain embodiments are directed to a surgical retractor with a frame having an adjustable circumference comprising four interconnecting frame segments. In certain aspects the outer edge of the frame segment has a series of ridges forming teeth or grooves along at least a portion of the length, and in certain aspects along the entire length of the outer edge. The frame segment can have a stop mechanism positioned at one or both ends of the frame segment. The stop can be in the form of a screw, pin, hole, or elevated material that can contact or engage a connector to stop the movement of the frame segment through the connector resulting in disassembly of the retractor. In certain aspects the stop is a screw that can engage threads formed in the face of a frame segment. In certain respects a surgical retractor comprises (a) a retractor frame having an adjustable circumference comprising (i) a plurality of curved frame segments, each frame segment comprising a first and second substantially straight arm portion and a curve portion there between where the long axis of the frame segment bends to form a rounded angle, each frame segment having a top and bottom face with an inner edge and an outer edge, wherein the frame segments are configured to overlap with a first arm portion of one frame segment overlapping a second arm portion of an adjacent frame segment, and (ii) connectors configured to receive arm portions of two adjacent frame segments to form the retractor frame, wherein the connector can be in (i) an unlocked configuration that allows the arm portions of the adjacent frame segments to move with respect to one another allowing the circumference of the frame to adjust or (ii) a locked configuration that fixes an arm portion at a position relative to an arm portion of the adjacent frame segment; and (b) two or more retractor blades coupled to the frame where the face of the retractor blade is substantially perpendicular to the plane of the frame. In certain aspects the connectors are designed to provide a ratchet mechanism. The ratchet mechanism of the connector is configured to interact with ratchet teeth that are position along all or a portion of the inner edge of the frame segments. In a further embodiment the connectors are configured to provide a space between the frame segments faces. The space between the frame segments can provide for the insertion of a portion of an attachment (e.g., a lip or protrusion on the attachment) to further stabilize additional attachments that may be affixed to the retractor. The ratchet mechanism allows the frame to be expanded when the connectors are in the locked position but does not allow the contraction of the frame. In certain aspects the ratchet mechanism associated with the connectors is a directional ratchet that allows a frame segment to move in one direction that results in expansion of the frame and resists or does not allow movement of the frame segment in the opposite direction, i.e., frame contraction. In a further aspect the edges of the ratchet teeth are beveled to allow for clearance of the ratchet. In certain aspects the retractor can be configured to be stabilized, coupled, or fixed to a subjects body, a wound, an incision, or a cavity. The retractor can be stabilized, coupled, or fixed by a clamp, suture, staple, or other mechanism. In certain aspects the retractor can have an adaptor or be fixed to an adaptor that in turn can be fixed to a support, such as a bed or operating table.

In another embodiment the connector is configured to allow the adjustment of the retractor blades up and down with respect to the frame segments. The connector can form a passage through which the proximal portion of the retractor blade can pass through. The passage being configured with a retractor blade locking mechanism that reversibly fixes the retractor blade at a particular position or depth. The locking mechanism can be a pin or a screw that can reversibly engage the proximal portion of the retractor blade to hold it in place when engaged and allow its movement when disengaged. In certain aspects the pin or screw can pass through an opening in the connector body or be attached to the top or bottom of the connector body. The proximal portion of the retractor blade can have an adjustment portion that passes through the connector. The adjustment portion can have grooves, holes, or teeth to engage the retractor blade locking mechanism.

In certain aspects the retractor frame is a rounded polygon, e.g., a triangle, quadrilateral (square, rectangle, rhombus, etc.), pentagon, hexagon or polygon. In a further aspect the frame is a rounded quadrilateral. In still a further aspect the frame is a rounded rectangle.

In certain aspects the outer edge, inner edge, or outer edge and inner edge of the frame segment is toothed along at least a portion of the segment. In a further aspect the top face, bottom face, or top and bottom face comprise a series of grooves or ridges.

In certain aspects the top, bottom, or top and bottom faces are planar. In a further aspect the top, bottom, or top and bottom faces are curved (concave or convex) along the short axis of the segment.

In certain aspects the frame segments are about 20, 25, 30, 35, 40, 45, 50, 60, 65, 70, 75, or 80 centimeters in length, including all values and ranges there between. In a further aspect a first arm portion of a segment is about 10 to 40 centimeters in length and a second arm portion is about 10 to 40 centimeters in length. In certain aspects the first and second arm portions are of equal length. The length of arm portion is measured from the end of the segment to beginning of the curve portion of the segment. In certain aspects the rounded angle of the frame segment is approximately 90 degrees or less. In a further aspect the arm portions of adjacent frame segments are positioned having the inner edge of one substantially straight arm portion aligned substantially parallel to the outer end of an adjacent frame segment. In another aspect the top face of one segment can face the bottom face of an adjacent segment. The frame segment faces can be in contact with each other or form a gap or space between the frame segments.

In certain aspects 2, 3, 4 or more retractor blades are coupled to the retractor frame. The retractor blade can have a distal blade portion and a proximal connector or adjustment portion. In a further aspect at least 2 retractor blades are coupled to the frame. In other aspects at least 4 retractor blades are coupled to the frame. In still a further aspect at least one retractor blade is coupled to a connector. In certain aspects at least one retractor blade is coupled to a frame segment. In a further aspect at least one retractor blade is configured to be moveable along the retractor frame. In still a further aspect the retractor blade is configured to be moveable up and down with respect to the retractor frame.

Certain embodiments are directed to a surgical retractor frame segment comprising a first and second substantially straight arm portion and a curve portion there between where the long axis of the frame segment bends to form an angle, each frame segment having a top and bottom face with an inner edge and an outer edge. The frame segment can further comprise an expansions stop that can be reversibly connected to the top or bottom face of the frame segment at or near one or both ends of the frame segment.

Other embodiments are directed to a surgical retractor connector comprising a body forming two lumens, each lumen configured to receive arm portions of two adjacent frame segments, a ratchet mechanism configured to interact with the inner edge of the frame segment when inserted into the connector lumen, wherein the connector can be in (i) an unlocked configuration that allows the arm portions of the adjacent frame segments to move with respect to one another allowing the circumference of the frame to adjust or (ii) a locked configuration that fixes an arm portion at a position relative to an arm portion of the adjacent frame segment. The connector can further comprise a retractor blade positioned below the frame and perpendicular to the plane of the frame. The retractor blade can be fixed to the connector body or removably connected to the connector body.

Certain embodiments are directed to methods of using the surgical retractor described herein, the method comprising: inserting a contracted retractor of claim 1 in a wound or incision, expanding the surgical retractor in one or more superior, inferior, or lateral direction to expose a body cavity, and locking the frame.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1A:
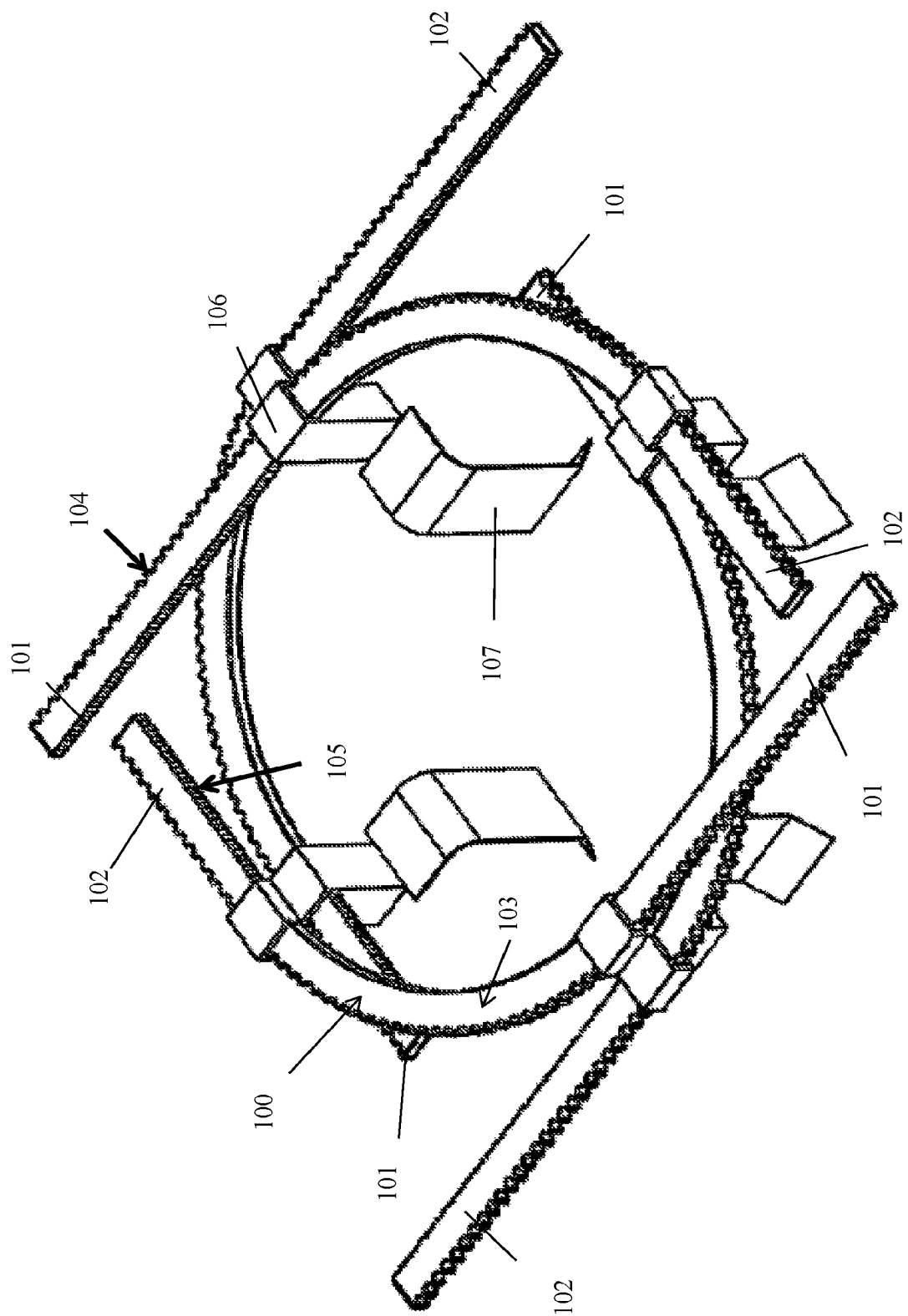
FIG. 1A is a perspective illustration of one embodiment of an adjustable retractor assembly in a collapsed configuration.

Attachment of the retractor described herein to an operating table or other support is not necessary, but can be an option, and therefore use of the retractor described herein does not require involvement of any non-sterile member of the operating team. In addition, the lack of an obtrusive fixed metal frame allows the surgeon increased mobility and positioning at the sides of the patient during the operation. The system remains sterile, and its simple and rapid deployment can be applied to emergency and time sensitive situations.

The adjustable/expandable system comprising multiple segments expanded on connectors or locking ratchet mechanisms allows full exposure of the surgical wound, as the multiple ratchet mechanisms attached to the ring segments allow the wound to be maximally retracted in both the transverse and longitudinal axes. This design allows the incision to be retracted to its maximal possible dimensions, as it is not limited by the use of a pre-determined ring size (as in the Bookwalter retractor). In addition, retraction of the wound edges in multiple directions (as opposed to only the transverse axis with the Balfour retractor) better engages the abdominal wall, allows for greater tension against the abdominal wall, and provides better stabilization of the retractor mechanism thereby improving surgical exposure. Lastly, the improved wound exposure obtained with retraction in multiple axes may reduce the necessary size of the incision required to obtain the same degree of exposure, thereby reducing scarring and unnecessary trauma to the tissues.

In addition to allowing maximal retraction of the incision in not only the transverse but also the longitudinal axes, the expandable locking circumferential frame system allows the subsequent attachment of multiple retractor blades to provide additional surgical exposure (similar to the Bookwalter retractor). The frame also allows the use of lighting options which attach directly to the frame, improving surgical visualization and illumination of deep wounds and/or spaces.

The surgical retractor comprises multiple frame segments forming a retractor frame by connecting adjacent segments with a connector. In certain aspects the retractor comprises four segments joined by four connectors. In certain embodiments a segment will have two arm portions joined by a curved portion. The segments are configured to be assembled to form a rounded polygon frame. In certain aspects the frame assembly can be a triangle, square, rectangle, pentagon, or other regular polygon. In certain embodiments the frame is a rounded rectangle, square, rhombus or irregular quadrilateral, which can depend on how each segment is positioned with respect to the adjacent segment. Each segment comprises a top and bottom surface/face with an inner edge facing the inside of the assembled frame and an outer facing outward.

FIGS. 1A-1E shows certain embodiments of an assembled retractor frame in a retracted or collapsed configuration. In certain embodiments the frame comprises four frame segments 100. Each segment 100 has two ends 101 and 102 connected by a connecting segment 103 (see also FIG. 5). The segments can have teeth 104 along one or more edges, and/or ridges or grooves along one or more face. In certain aspects the inner edge of segment 100 is configured to interact with a ratchet mechanism (112 and 113), portions of segment 100 can have ratchet teeth 105. The inner edge faces the interior of the opening formed by assembly of segments 100. In other aspects segment 100 can have notches, grooves, or teeth 104 that can be utilized for securing attachments and the like. In certain aspects notches, grooves, or teeth can be positioned in the outer edge of segment 100, the upper face of segment 100, the lower face of segment 100, or combinations thereof. Segment ends 101 and 102 can be connected by connector 106. In certain embodiments connector 106 comprises a ratchet mechanism that interacts with ratchet teeth 105 to adjustably secure segment ends 101 and 102 and allowing expansion and contraction of the assembled frame as well as stabilizing the frame once a desired configuration is achieved. In certain aspects connector 106 can have a fixed or removable retractor blade 107. In certain aspects the frame segment 100 has an expansion stop 117. The expansion stop can be a screw, a clip, a pin, or other mechanism that is configured to not allow the frame segment to pass through connector 106.

Figure 1B:
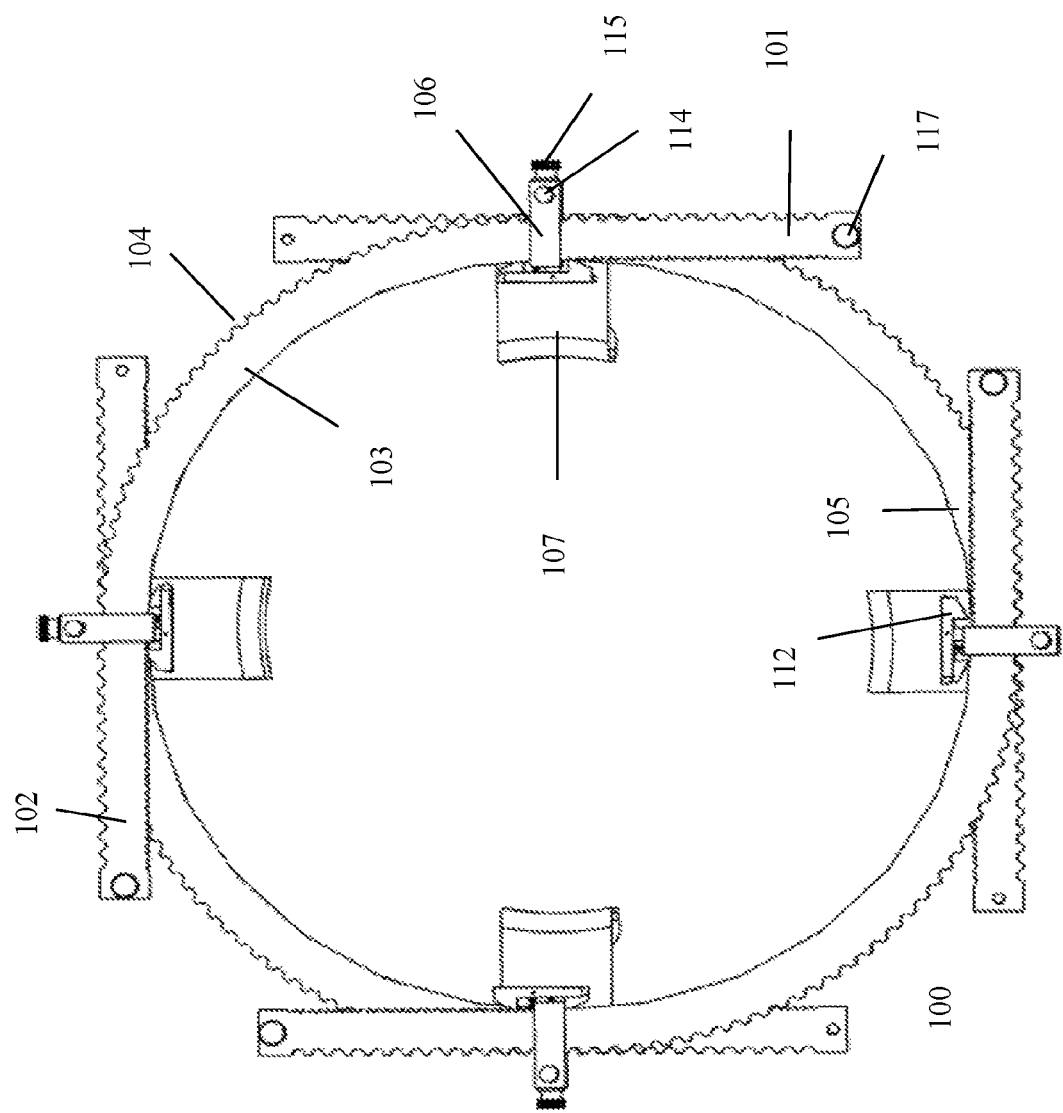
FIG. 1B is a top-down illustration of a second embodiment of an adjustable retractor assembly in a collapsed configuration.
Figure 1C:
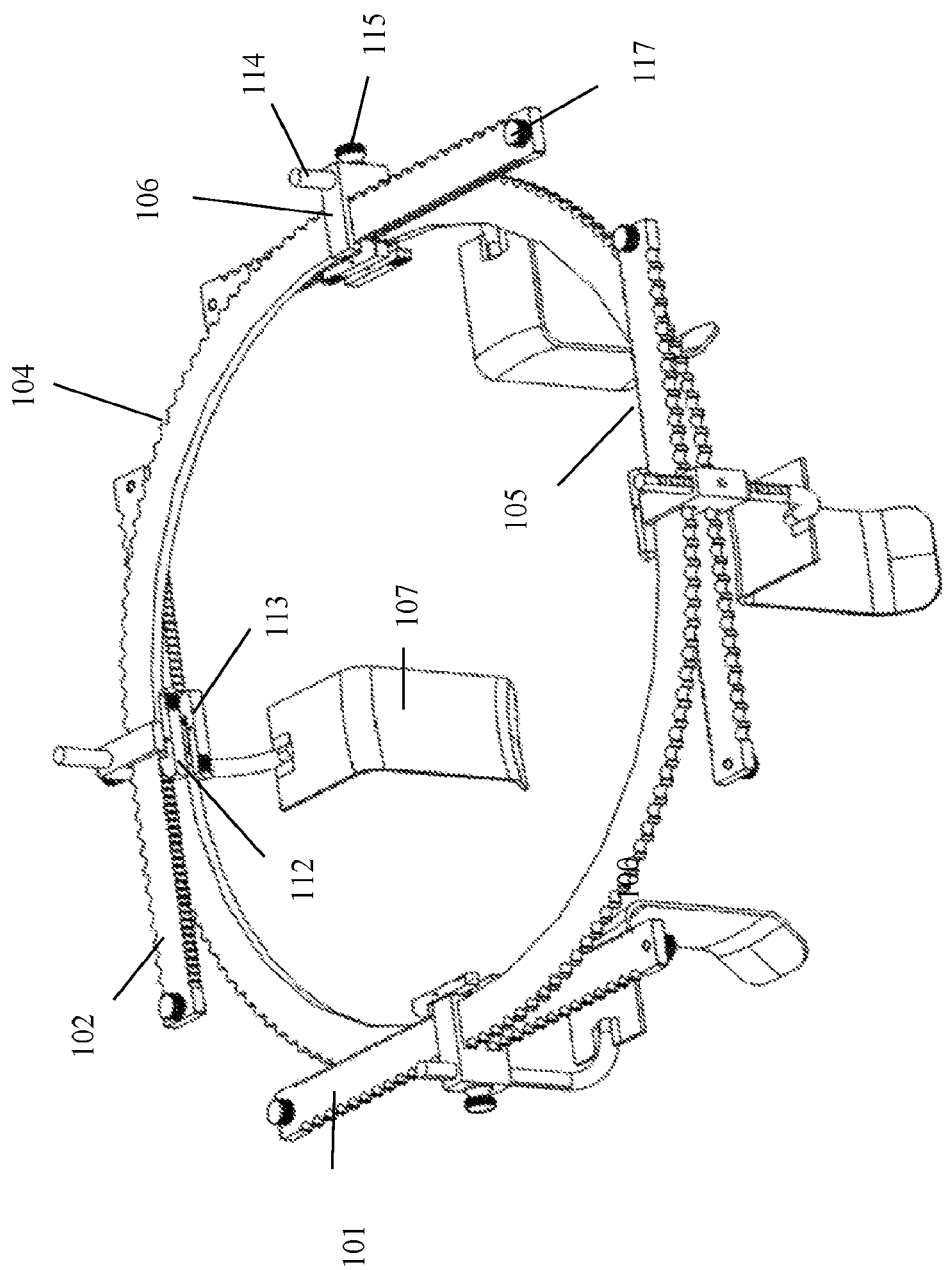
FIG. 1C is a perspective illustration from the top of the second embodiment of an adjustable retractor assembly in a collapsed configuration.
Figure 1D:
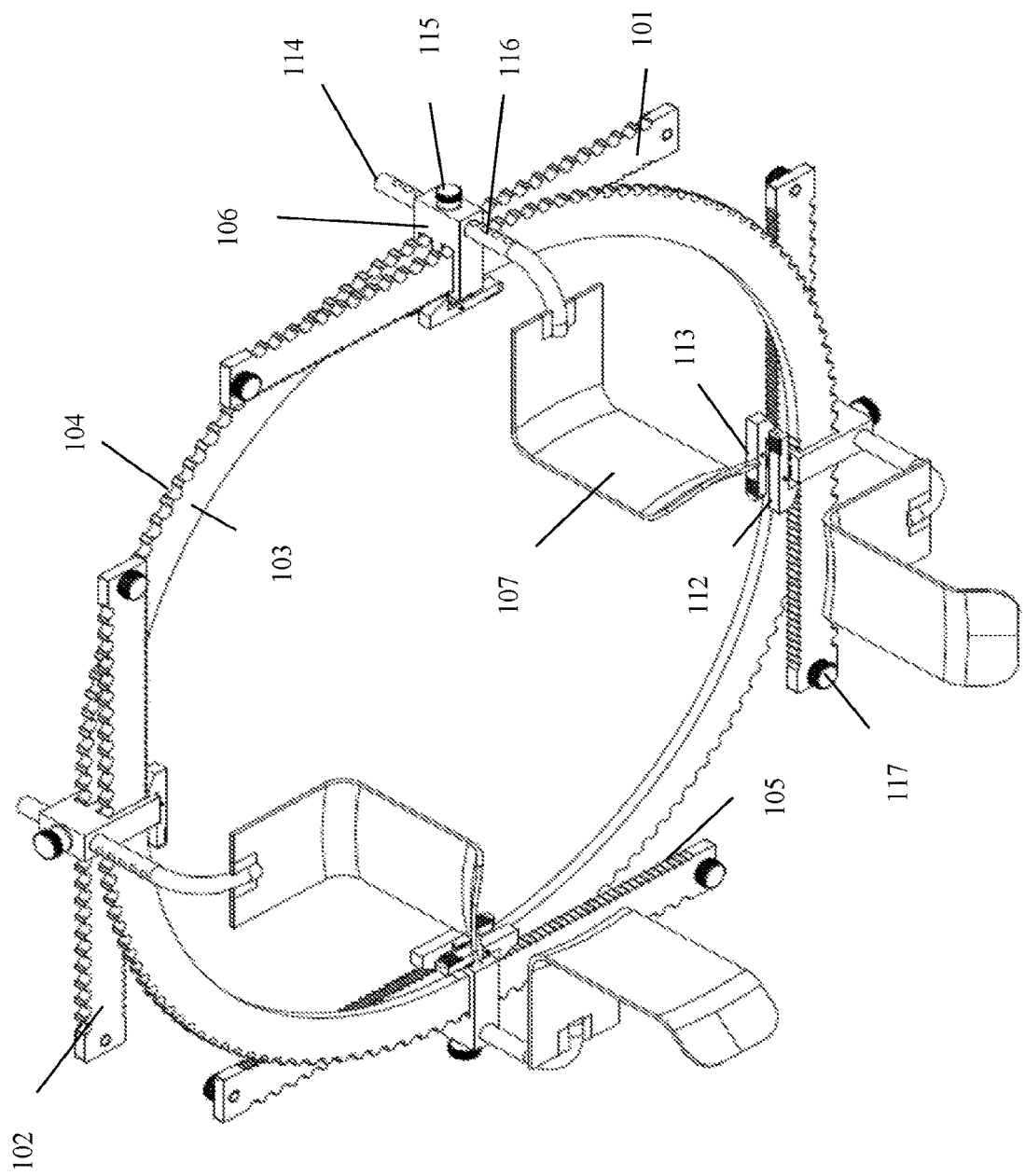
FIG. 1D is a perspective illustration from the bottom of the second embodiment of an adjustable retractor assembly in a collapsed configuration.
Figure 1E:
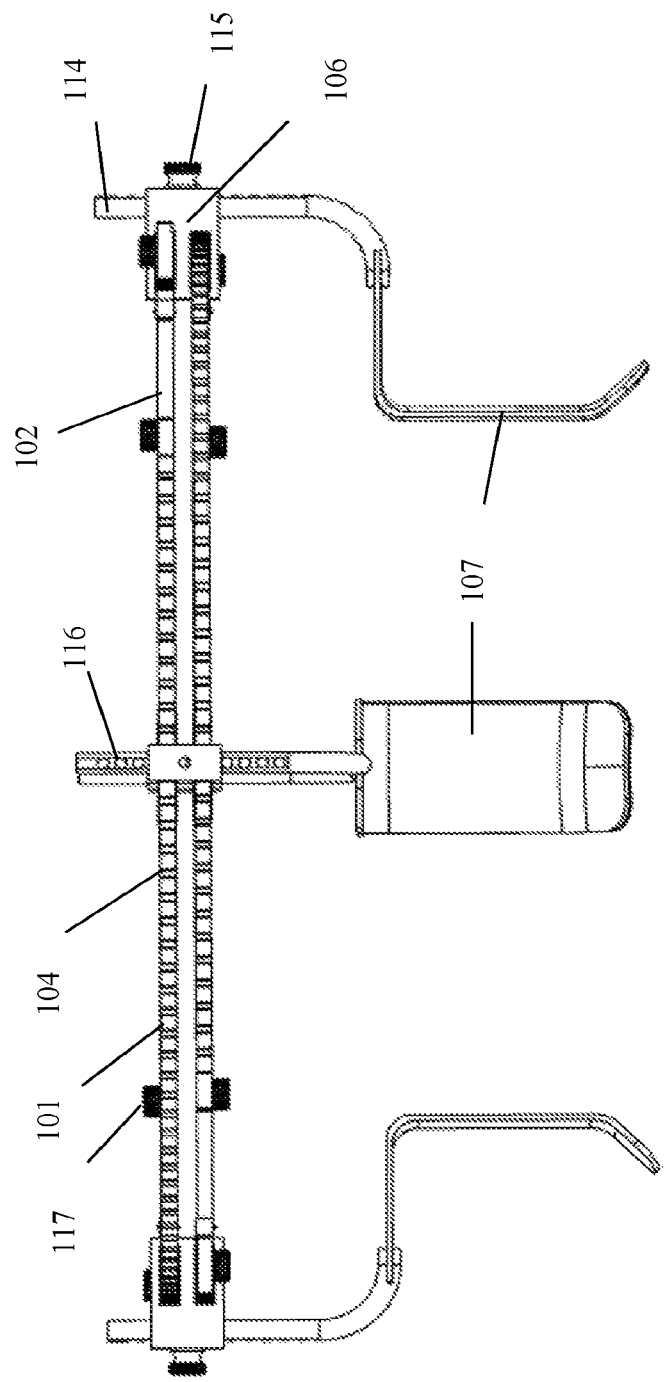
FIG. 1E is a side illustration of a second embodiment of an adjustable retractor assembly in a collapsed configuration.
Figure 2A:
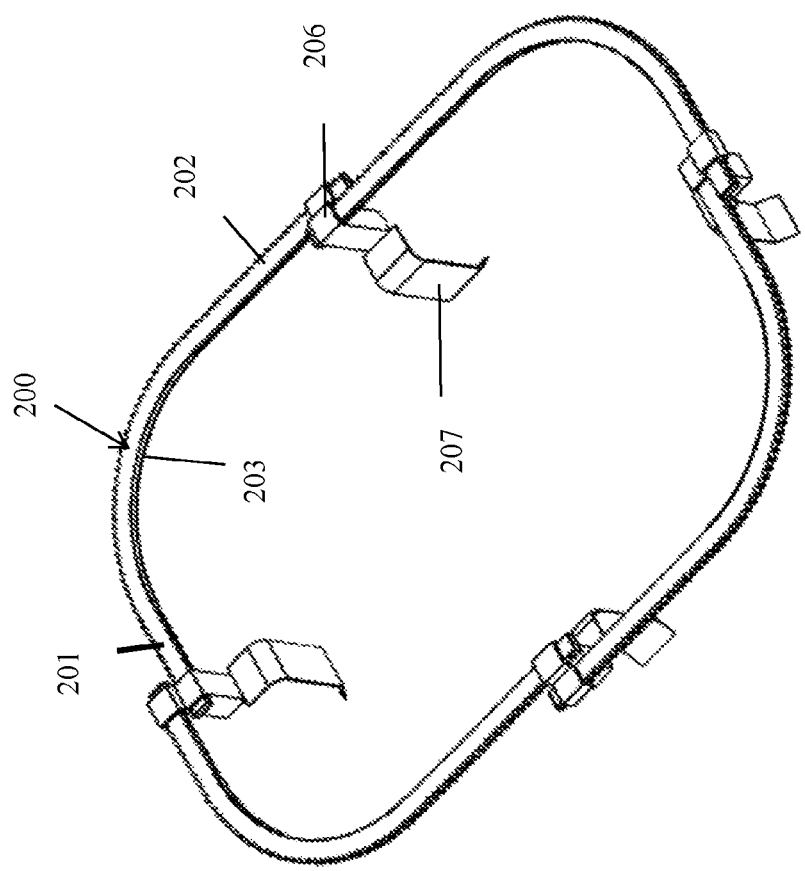
FIG. 2A is a perspective illustration of one embodiment of an adjustable retractor assembly in an expanded configuration.
Figure 2B:
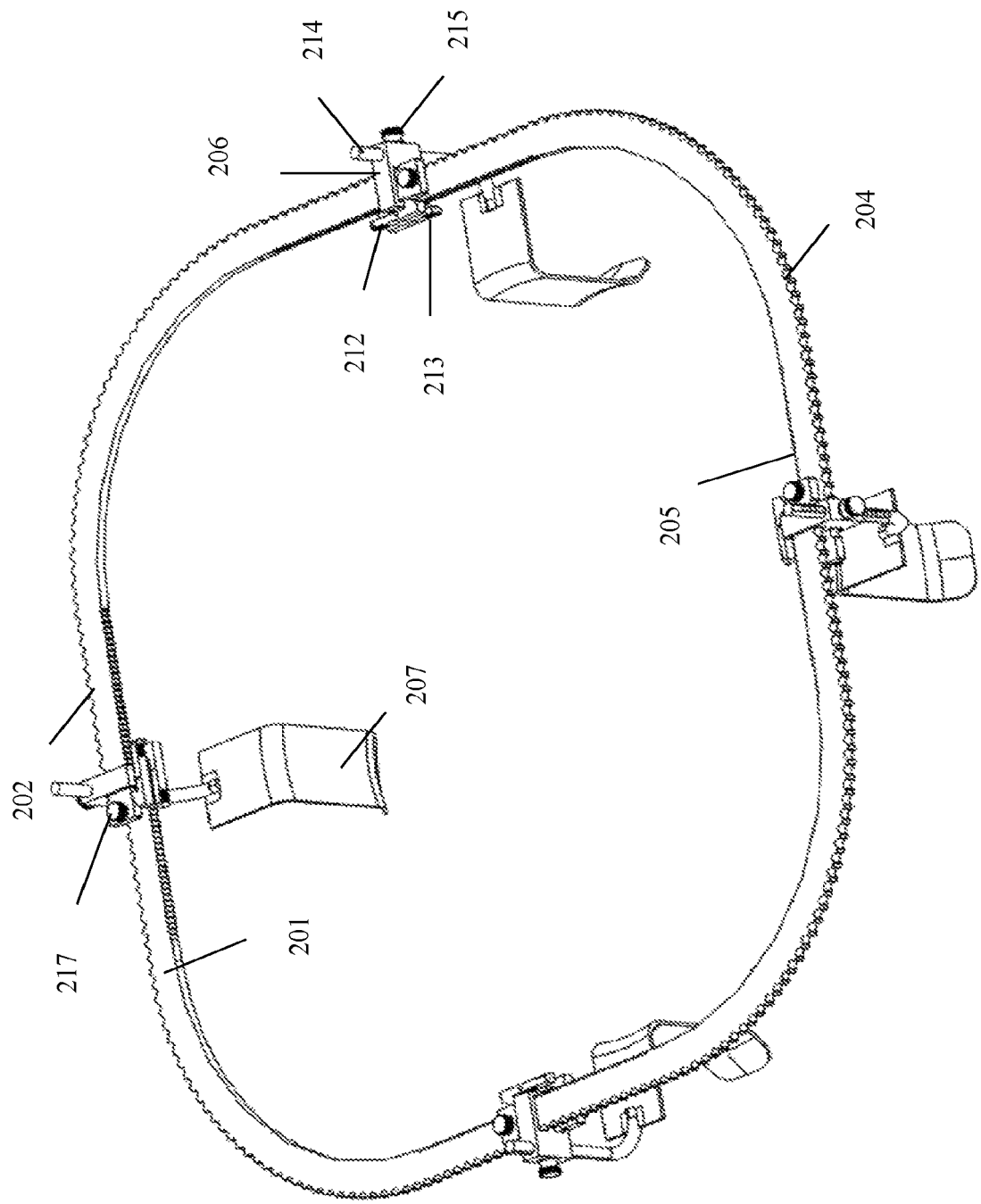
FIG. 2B is a perspective illustration of a second embodiment of an adjustable retractor assembly in an expanded configuration.
Figure 2C:
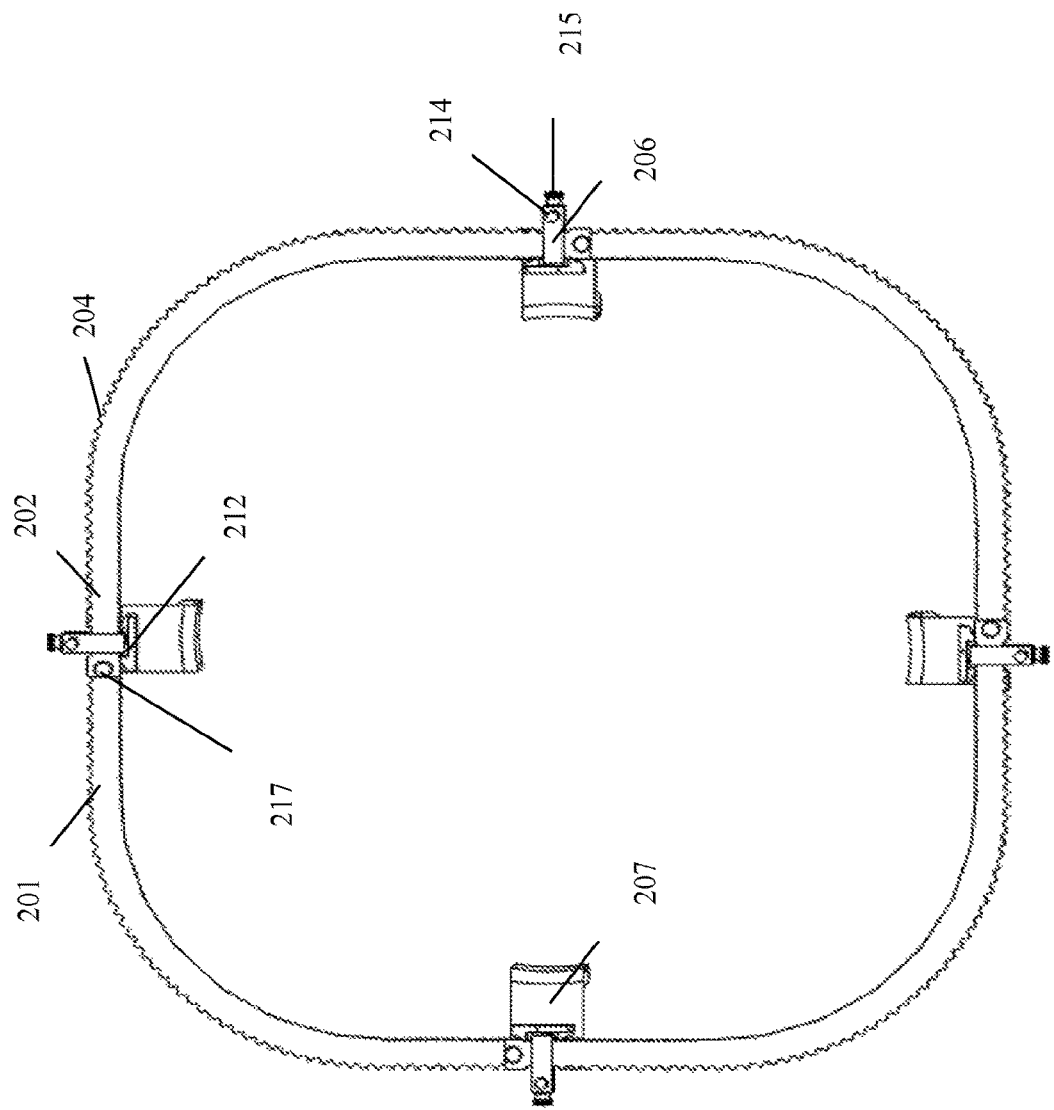
FIG. 2C is a top-down illustration of the second embodiment of an adjustable retractor assembly in an expanded configuration.
Figure 3A:
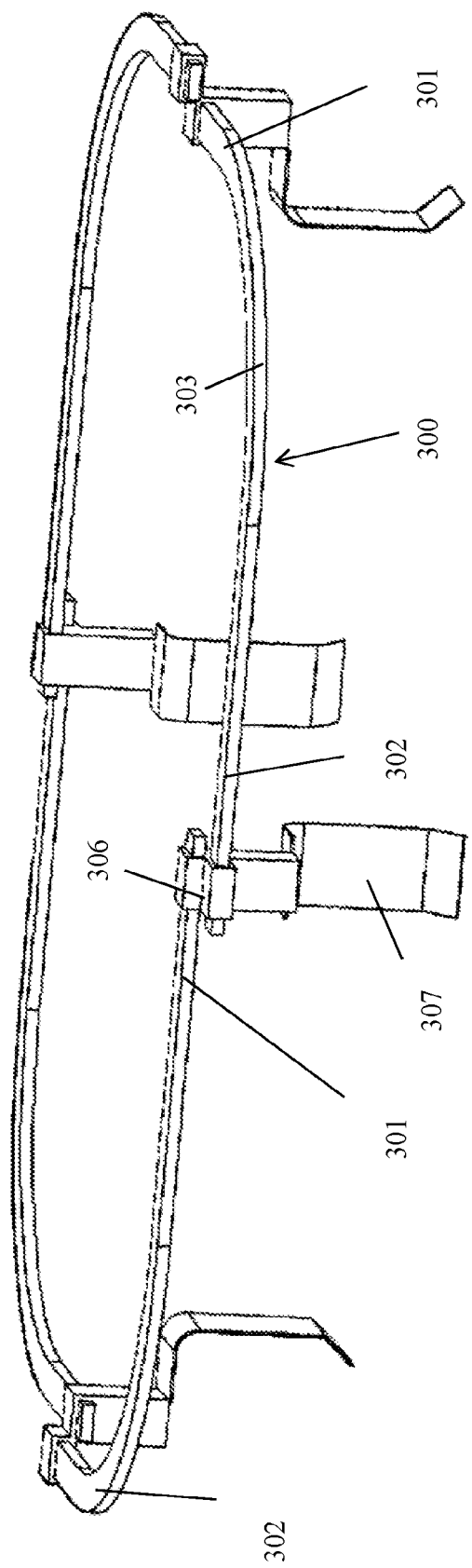
FIG. 3A is a perspective illustration of one embodiment of an extended retractor.
Figure 3B:
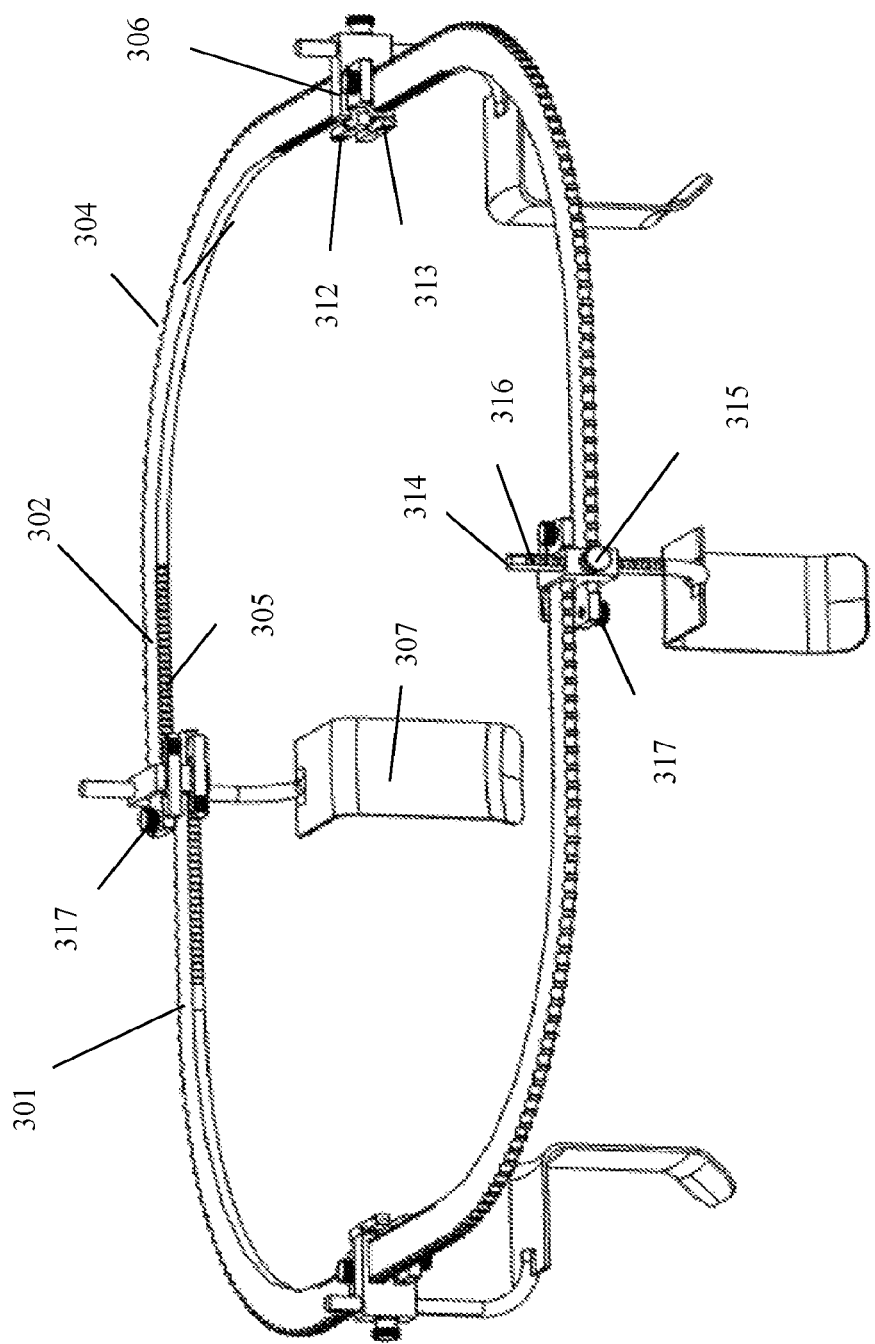
FIG. 3B is a perspective illustration of a second embodiment of an extended retractor
Figure 3C:
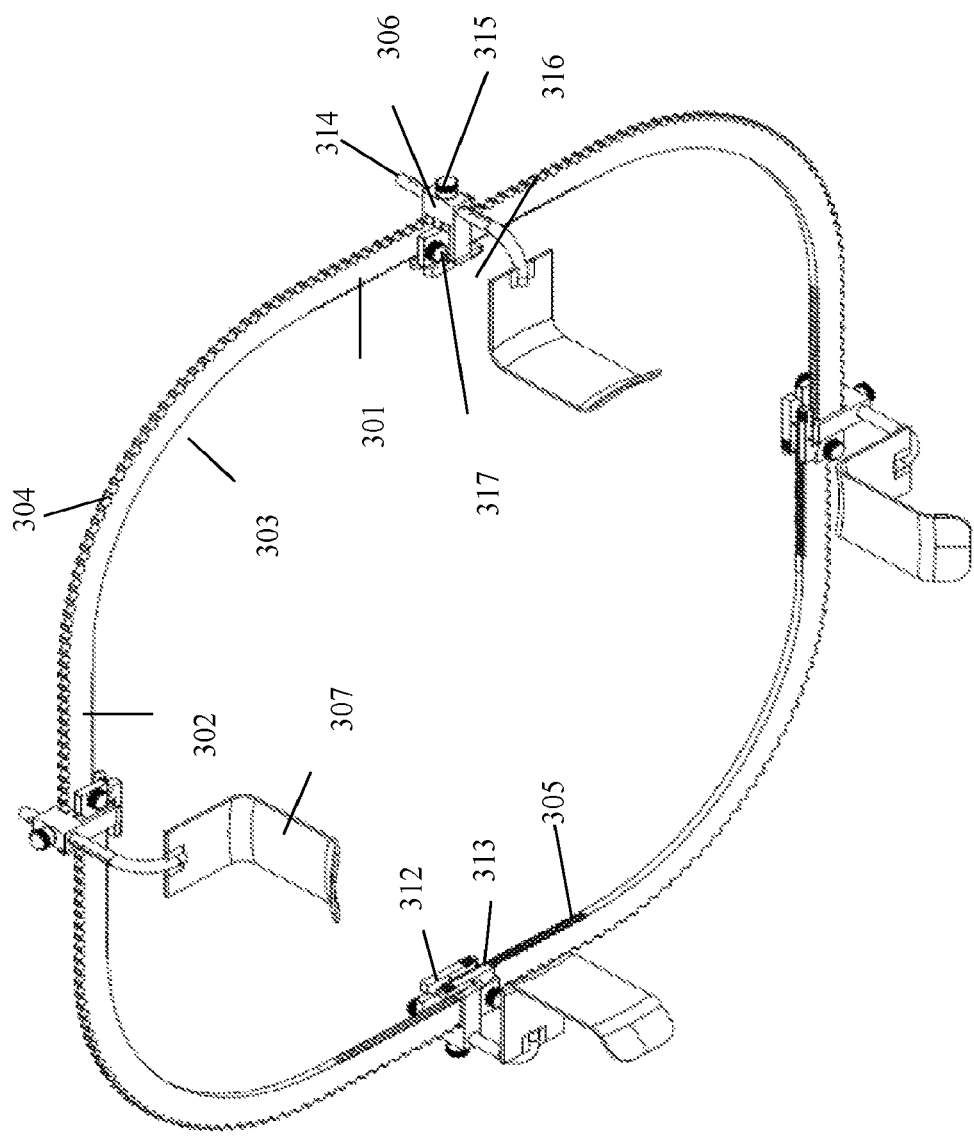
FIG. 3C is a perspective view from the bottom of a second embodiment of an extended retractor.
Figure 3D:
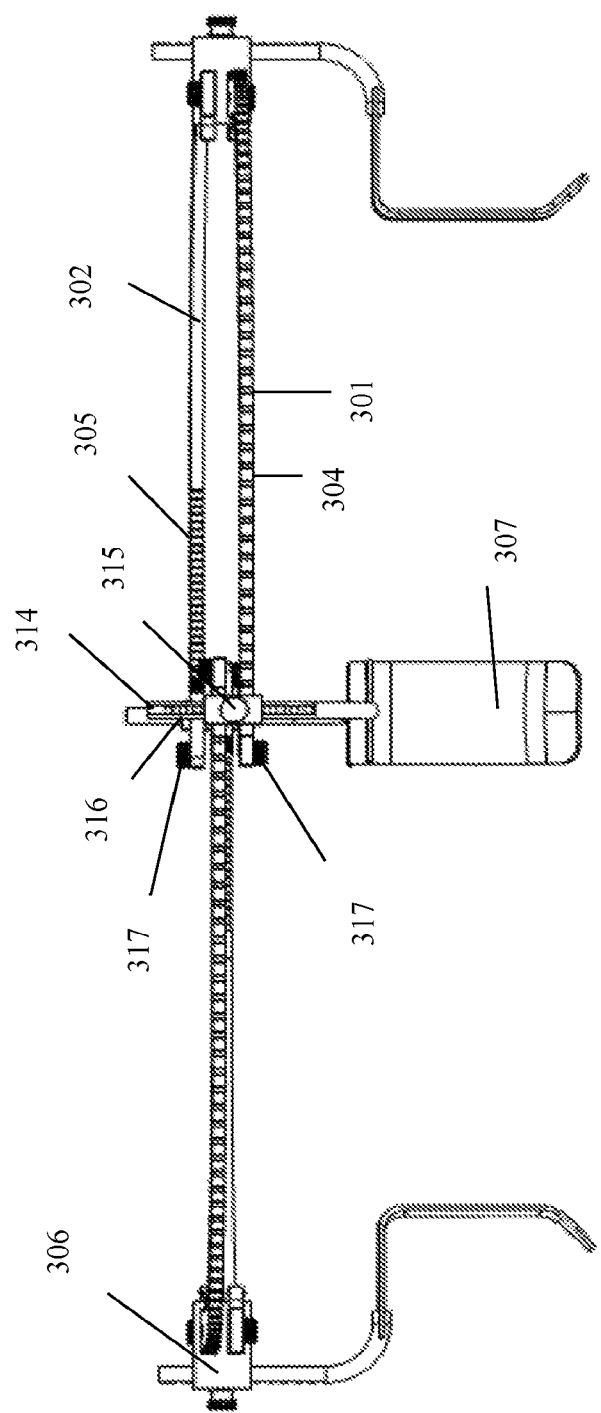
FIG. 3D is a side view illustration of a second embodiment of an extended retractor

Referring to FIGS. 1B to 1D show an embodiment of the invention where the retractor blades can be moved up and down with respect to the frame. In this embodiment the connector is configured to provide for movement of retractor blade 107. Connector 106 is configured to receive the proximal portion of the retractor blade 114. The proximal portion of the retractor blade 114 is reversibly locked by using retractor blade locking mechanism 115. The proximal portion of the retractor can form a retractor blade locking mechanism receiver 116. The locking mechanism receiver 116 can be a notch, a hole, a cavity or other structure to receive the locking mechanism 115. When the locking mechanism is engaged the retractor blade is reversibly fixed at that particular position. If one wanted to adjust the retractor blade one would disengage locking mechanism 115, move the retractor blade 107 to a new position, and fix that position by engaging locking mechanism 115 with the locking mechanism receiver 116.

FIG. 2A-2C and FIG. 3A-3D show an assembled retractor frame in an expanded configuration. Connector 106, 206, 306 are configured with a release/locking mechanism that allows a person to release segment 100, 200, 300 and allow expansion or contraction of the frame as well as providing a locking mechanism to secure the segments in place when desired. In certain aspects connectors 106, 206, 306 comprise a locking, ratchet mechanism (see also FIG. 4 and FIG. 6). In another embodiment the frame segment has a stop mechanism that will stop the expansion of the frame at a certain point. The expansion stop 217, 317 is an elevated portion that cannot pass through the connector resulting the stopping of the frame expansion at the point to the expansion stop 21,317. Expansion stop 217, 317 can be a screw or a pin that can be engaged or disengaged as needed. Typically the expansion stop would be engaged during use to prevent over extension. FIG. 2B-2C and FIG. 3B-3C show an embodiment where not only does the frame have a mechanism for adjustment, but so does the retractor blade portion of the device. The retractor blade can have a portion that is proximal to the frame (proximal portion 214, 314) that passes through next to the connector and can engage a retractor blade locking mechanism 215, 315 to be reversibly fixed in position. Reversibly fixed means that it will maintain its position until a locking mechanism is disengaged or the engagement is reversed allowing freedom of movement when disengaged. In certain aspects the proximal portion can have one or more locking mechanism receivers 216, 316 which receive the locking mechanism.

Figure 4:
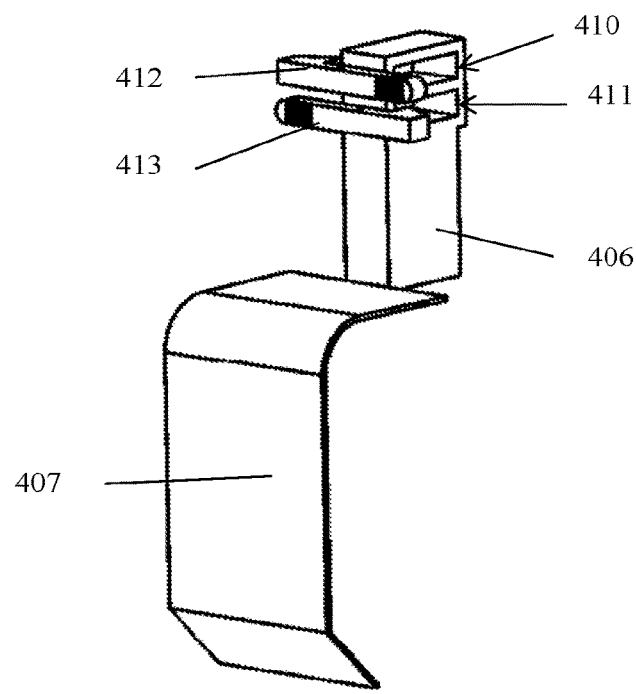
FIG. 4 is an illustration of one embodiment of a connector.

FIG. 4 shows one embodiment of connector 106, 206, 306 in isolation. Each connector 106, 206, 306 can have two receiving openings, a top opening 410 and a bottom opening 411 for receiving the ends of two adjacent segments, e.g., 101 and 102. In certain aspects opening 410 and 411 can be offset, stacked, or side-by-side. In certain aspects the openings are offset. In other aspects the openings are stacked. In certain aspects a connector has 1 (e.g., when a connector is a fixed, integral part of one end of a frame segment), 2, or more openings. In certain embodiments one frame segment is attached to two consecutive connectors, for example, when the connector has 2 openings, a first frame segment is attached to a first opening in a first connector and a first opening in a second connector, the second connector can be attached to an adjacent frame segment. The adjacent frame segment is attached through the second opening in a shared connector (second connector) and a second opening of the non-shared connector (third connector) and so forth until a retractor is formed. Connector 406 can comprise ratchets 412 and 413, which are configured to ratchet in opposite directions. Ratchets 412 and 413 can be configured to interact with a toothed surface of two adjacent segments (e.g., see FIG. 5 part 505). The ratchets can be configured to allow the frame to be expanded by applying a force away from the centerpoint of the retractor without disengaging the ratchet. In other aspects the ratchet is configured to not allow contraction of the frame unless the ratchet is disengaged. Other release/locking mechanisms can be integrated into the current design, so the ratchet mechanism is just one example. The position of the connector along a segment can be fixed by engaging a lock mechanism that can engage the teeth or grooves for locking purposes. In other embodiments the connector can be integrated into one end of the frame segment, in this case the connector may only have one opening and one ratchet mechanism since the connector is fixed at one end of the segment. A retractor blade need not be associated with the connector. A retractor blade or other implement can be fixed to one or more connector or can be an accessory implement that attaches to the frame at positions other than the connector points. A plurality of retractor blades or other implements can be attached to the frame, in certain aspects 2, 3, 4, 5, 6, 7, 8, 9, 10 or more retractor blades and/or other implements can be attached to the frame. The only limiting factor for attachment is the space available along the frame and physical interference between attachments.

Figure 5:
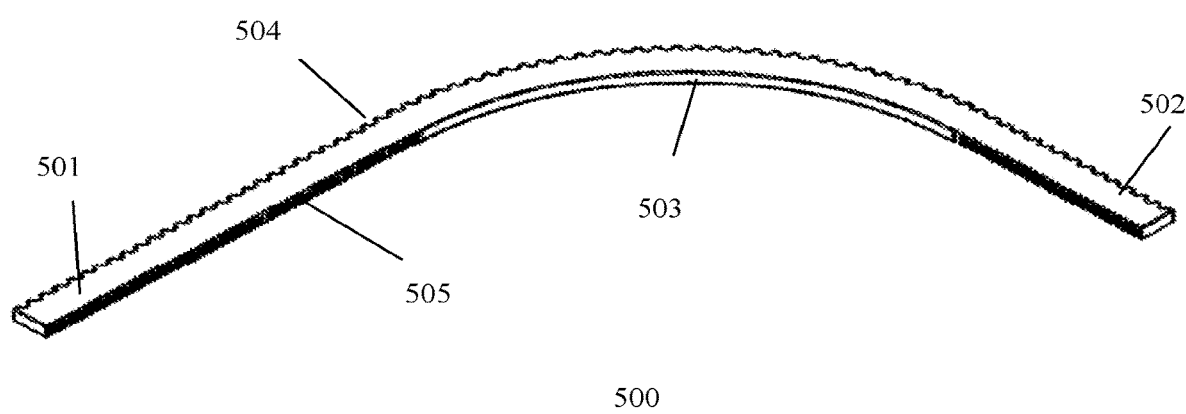
FIG. 5 is an illustration of a frame segment.

FIG. 5 shows an illustration of a frame segment in isolation. Frame segment 500 comprises various regions or portions. Frame segment 500 has first end 501 and second end 502. Each end of frame segment 500 is configured to interact with a connector in a way that allows assembly and adjustment of the assembled frame of the retractor. The inner edge of the ends can be configured to allow connector release/locking. In certain aspects the outer edge can be configured to interact with the connector, alone or in combination with the inner edge. Connecting segment 503 is the portion of the frame segment between end 501 and 502. Connecting segment 503 provides for angle to be formed between the ends and allow a plurality of frame segments to be positioned with respect to each other in order to form a closed retractor frame with each segment being connected by a connector. In certain aspects connecting segment 503 is in the form of a curve or an angle. The connecting segment can be characterized by the angle formed between the long axis of end 501 and 502 (segment angle). In certain aspects this segment angle is between 45 and 180 degrees. In certain aspects the segment angle is or is about 90 degrees.

Figure 6A:
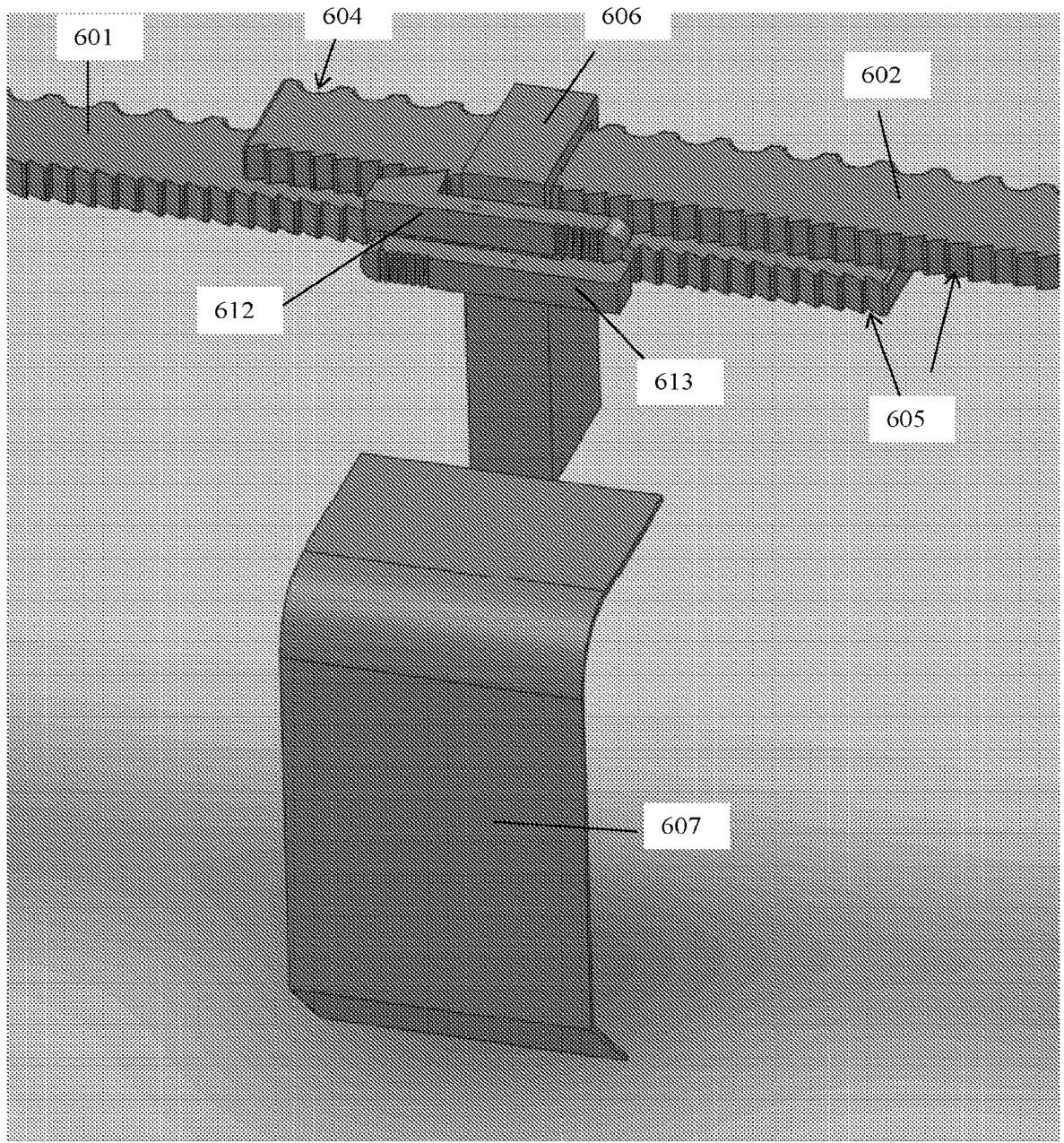
FIG. 6A is an illustration of one embodiment for a segment/connector assembly.
Figure 6B:
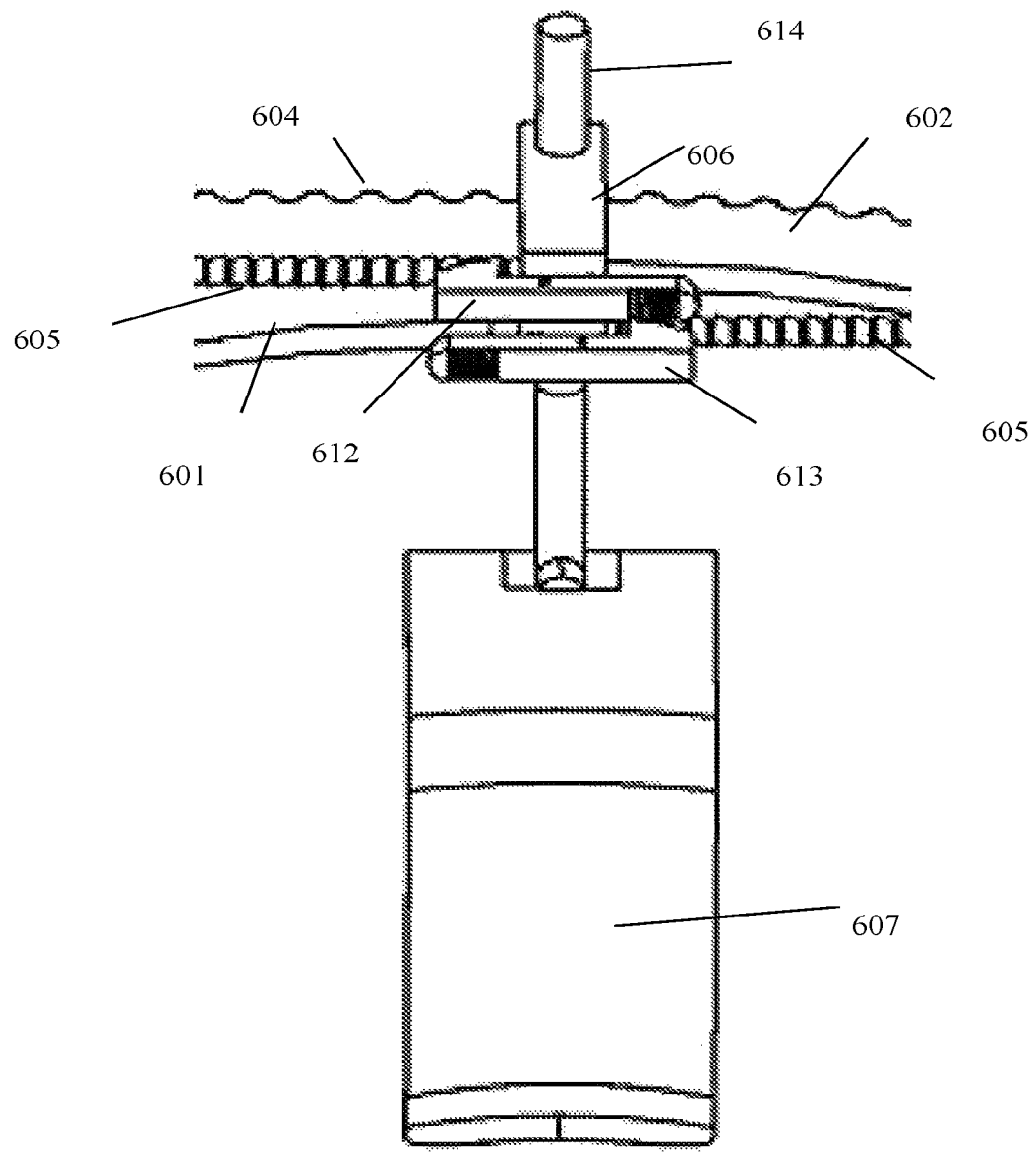
FIG. 6B is an illustration of a second embodiment for a segment/connector assembly.

FIGS. 6A and 6B illustrate embodiments of a connector assembly connecting two adjacent frame segments. In FIG. 6A, this particular embodiment shows frame segments 600 being positioned in opening in connector 606. Connector 606 being configured with ratchet 612 and 613. Each frame segment 600 has ratchet teeth 605 being angle in opposing directions with respect to the long axis of the frame segment ends. The ratchet mechanism can be disengaged by pressing the ratchet at the end opposite the ratchet, pivoting the ratchet away from contacting the ratchet teeth and allowing movement of the frame segment in either direction. FIG. 6B illustrates an embodiment where the retractor blade can be adjusted using the adjusting mechanism incorporated into connector 606 and the proximal portion of the retractor blade 614.

Figure 7:
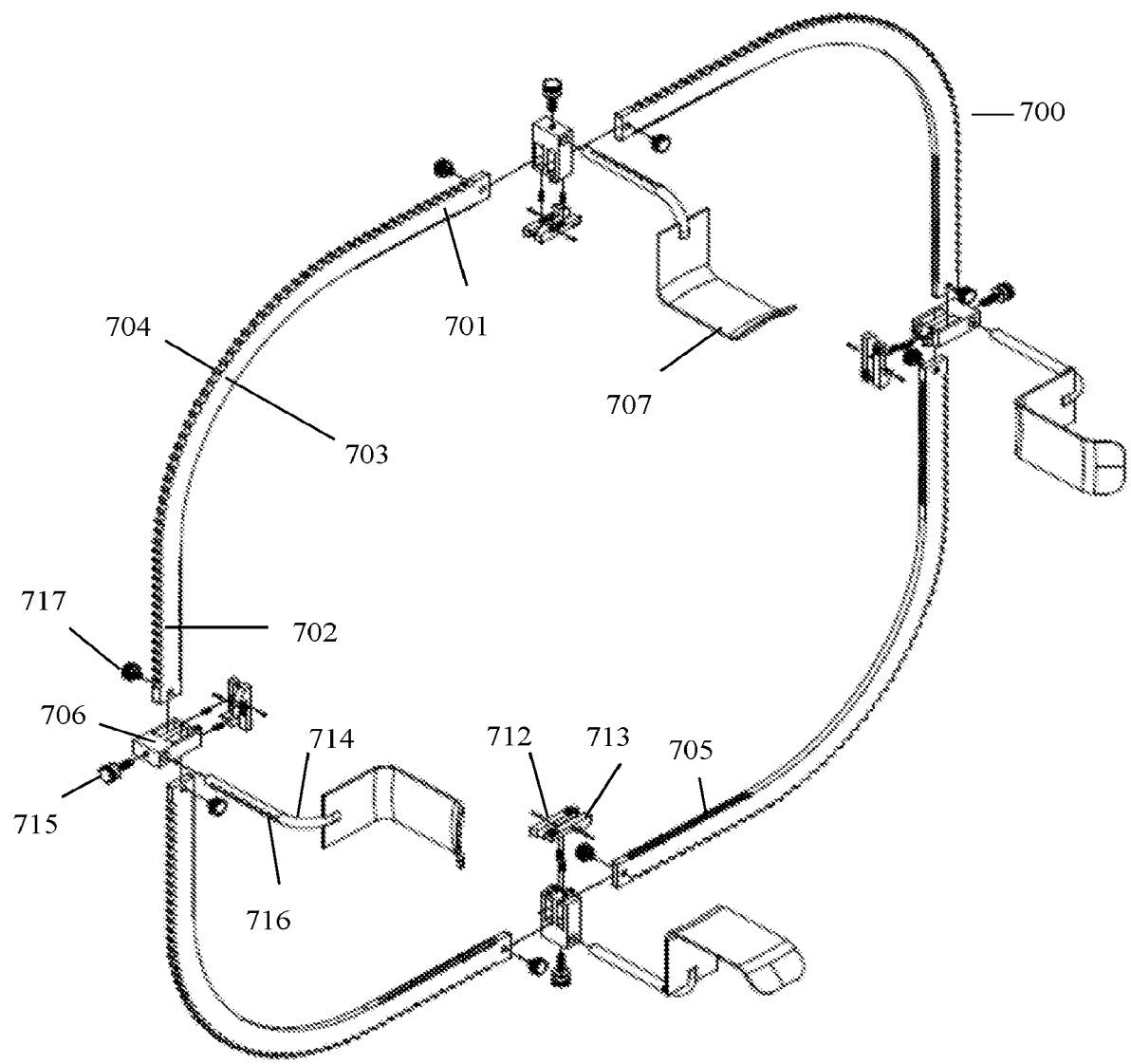
FIG. 7 is an exploded view of one embodiment of the surgical retractor.

FIG. 7 illustrated an exploded view of the surgical retractor. Shown are frame segments 700 having a first end 701 and a second end 702 connected by a curved portion 703. The outer edge of segment 700 having grooves 704 and the inner edge having ratchet teeth 705. Also shown are connector 706, ratchet arm 712 and 713, expansion stop 717, retractor blade 707, retractor blade arm 714 with receiving mechanisms 714, retractor blade locking mechanism 715.

The segment, connector, and retractor blade can be metallic, metallic alloy, plastic, or combination thereof. In certain aspects the retractor is made of material that can be autoclaved or otherwise sterilized (e.g. irradiated, etc.). The frame segment can be a formed rod (having a bend or angle) with circular, oval, square, or rectangular cross section. The connectors are configured to receive and reversibly engage the frame segments and connecting adjacent segments in the frame. The segments are coupled connectors to form a retractor frame. Each connector couples two segments.

What is claimed is:

1. An adjustable surgical retractor comprising, a retractor frame having an adjustable perimeter comprising:
   a plurality of frame segments, each frame segment having a long axis and a plurality of arm portions, the plurality of arm portions comprising a first straight arm portion and a second straight arm portion, and a curve portion extending between the first straight arm portion and the second straight arm portion, where the long axis of the frame segment bends at the curve portion to form an angle between the first straight arm portion and the second straight arm portion, each frame segment having a top and bottom face with an inner edge and an outer edge, each frame segment forming a series of notches or teeth extending continuously along the curve portion between the first straight arm portion and the second straight arm portion, the curve portion being configured to receive at least one of a plurality of retractor blades at any point along the curve portion, and
   a plurality of connectors, each connector being configured to receive a straight arm portion of each of two adjacent frame segments when the straight arm portions are parallel to form at least a portion of the retractor frame, wherein each connector can be in (i) an unlocked configuration that allows movement of the received arm portions of the adjacent frame segments with respect to one another, thereby allowing the retractor frame to expand or contract by adjustment of a perimeter of the retractor frame or (ii) a locked configuration that restricts the movement of the received arm-portions of the adjacent frame segments with respect to one another, thereby restricting at least one of expansion and contraction of the retractor frame; and
   the plurality of retractor blades coupled to the retractor frame where the coupling of at least one the plurality of retractor blades engages the series of notches or teeth along the curve portion.

2. The retractor of claim 1, wherein the frame segments each further comprise an expansion stop at one end of the frame segment that is configured to stop expansion of the retractor frame prior to a frame segment passing completely out of the connector.

3. The retractor of claim 1, wherein at least one of the arm portions further comprises a removable expansion stop coupled with a prescribed slot or pattern of holes formed in the frame segment that together are configured to stop expansion of the retractor frame prior to the frame segment passing completely out of a connector.

4. The retractor of claim 1, wherein at least one of the connectors when in the locked configuration does not allow the retractor frame to be expanded or contracted.

5. The retractor of claim 1, wherein at least one of the connectors is configured to position the ends of the adjacent frame segments in a stacked configuration.

6. The retractor of claim 1, wherein at least one of the connectors is configured to position the ends of the adjacent frame segments in an offset configuration.

7. The retractor of claim 1, wherein the retractor frame is a rounded polygon.

8. The retractor of claim 1, wherein the retractor frame is a rounded quadrilateral.

9. The retractor of claim 1, wherein the arm portions of adjacent frame segments are positioned having the inner edge of one straight arm portion aligned parallel to the outer end of an adjacent frame segment.

10. The retractor of claim 1, wherein the arm portions are 10 to 30 centimeters in length.

11. The retractor of claim 1, wherein the angle between the first straight arm portion and the second straight arm portion is approximately 90 degrees.

12. The retractor of claim 1, wherein the plurality of retractor blades comprise 2, 3, or 4 retractor blades are coupled to the retractor frame.

13. The retractor of claim 1, wherein the plurality of retractor blades comprise 2, 3, or 4 retractor blades are configured to be decoupled from the retractor frame.

14. The retractor of claim 1, wherein at least one retractor blade is coupled to a connector.

15. The retractor of claim 1, wherein at least one retractor blade is coupled to the frame segment at one of the plurality of arm portions.

16. The retractor of claim 15, wherein at least one retractor blade is configured to be moveable along the curve portion of each frame segment.

17. The retractor of claim 1, wherein the retractor is coupled to a bed frame.

18. The retractor of claim 1, wherein the retractor frame is configured to be attached to patient solely by the plurality of retractor blades after being expanded.

19. A method of using the surgical retractor of claim 1, comprising:
coupling a plurality of retractor blades on the frame of the retractor, at least one of the blades being coupled to the curve portion of a frame segment of the frame;
inserting the retractor blades of the retractor of claim 1 in a wound or incision of a patient body; and
expanding the surgical retractor in one or more superior, inferior, or lateral direction to engage the retractor blades with the patient body and expose a body cavity; and
locking the connectors so as to prevent contraction of the frame.

20. The retractor of claim 1 the plurality of frame segments being four segments.

21. An adjustable surgical retractor comprising, a retractor frame having an adjustable perimeter comprising:
a plurality of frame segments, each frame segment having a long axis and a plurality of arm portions, the plurality of arm portions comprising a first straight arm portion and a second straight arm portion, and a curve portion extending between the first straight arm portion and the second straight arm portion, where the long axis of the frame segment bends at the curve portion to form an angle between the first straight arm portion and the second straight arm portion, each frame segment having a top and bottom face with an inner edge and an outer edge; and
a plurality of connectors, each connector being configured to receive at least one of the plurality of arm portions of two adjacent frame segments to form the retractor frame, wherein each connector can be in (i) an unlocked configuration that allows movement of the received arm portions of the adjacent frame segments with respect to one another, thereby allowing the retractor frame to expand or contract by adjustment of a perimeter of the retractor frame or (ii) a locked configuration that restricts the movement of the received arm-portions of the adjacent frame segments with respect to one another, thereby restricting at least one of expansion and contraction of the retractor frame; and
a plurality of retractor blades, each of the plurality of retractor blades being coupled to the retractor frame by one of said plurality of connectors, wherein the face of each of the plurality of retractor blades is perpendicular to and below a plane of the retractor frame;
each of the plurality of retractor blades being adjustably coupled to a connector among the plurality of connectors, said connector being configured to translatably receive a proximal portion of a retractor blade coupled thereto and to reversably fix a position of said retractor blade with a locking mechanism incorporated into said connector, wherein the proximal portion of said retractor blade is translatable in said connector so as to move said retractor blade up and down until locked by a retractor blade locking mechanism.

22. A surgical retractor frame segment comprising:
a plurality of arm portions, the plurality of arm portions comprising a first straight arm portion and a second straight arm portion and a curve portion there between where the long axis of the frame segment bends to form an angle between the two arm portions, the frame segment having a top and bottom face with an inner edge and an outer edge, the outer edge of each frame segment forming a series of notches or teeth extending continuously along the curve portion between the first straight arm portion and the second straight arm portion, the curve portion being configured to receive at least one of a plurality of retractor blades at any point along the curve portion; and
a connector coupled to a straight arm portion of the plurality of arm portions, the connector being configured to receive, when placed in parallel with the arm portion to which the connector is coupled, an arm portion of a separate surgical retractor frame segment, wherein the connector can be in (i) an unlocked configuration that allows movement of the received arm portion with respect to the arm portion to which the connector is coupled, or (ii) a locked configuration that restricts the movement of the received arm portion with respect to the arm portion to which the connector is coupled.

23. The frame segment of claim 22, further comprising an expansion stop that can be reversibly connected to the frame segment at or near one or both ends of the frame segment.

24. An adjustable surgical retractor comprising, a retractor frame having an adjustable perimeter comprising:
a plurality of frame segments, each frame segment having a long axis and a plurality of arm portions, the plurality of arm portions comprising a first straight arm portion and a second straight arm portion, and a curve portion extending between the first straight arm portion and the second straight arm portion, where the long axis of the frame segment bends at the curve portion to form an angle between the first straight arm portion and the second straight arm portion, each frame segment having a top and bottom face with an inner edge and an outer edge;
the plurality of frame segments being four frame segments; and
a plurality of connectors, each connector being configured to receive at least one of the plurality of arm portions of two adjacent frame segments to form the retractor frame, wherein each connector can be in (i) an unlocked configuration that allows movement of the received arm portions of the adjacent frame segments with respect to one another, thereby allowing the retractor frame to expand or contract by adjustment of a perimeter of the retractor frame or (ii) a locked configuration that restricts the movement of the received arm portions of the adjacent frame segments with respect to one another, thereby restricting at least one of expansion and contraction of the retractor frame; and
a plurality of retractor blades coupled to the retractor frame, wherein a face of each of said plurality of retractor blades is perpendicular to the plane of the retractor frame.

25. The retractor of claim 24, wherein at least one of the arm portions further comprises a removable expansion stop coupled with a prescribed slot or pattern of holes formed in the frame segment that together are configured to stop expansion of the frame prior to the frame segment passing completely out of a connector.

26. The retractor of claim 24, wherein at least one of the connectors when in the locked configuration does not allow the retractor frame to be expanded or contracted.

27. The retractor of claim 24, wherein at least one of the connectors is configured to position the ends of the adjacent frame segments in a stacked configuration.

28. The retractor of claim 24, wherein at least one of the connectors is configured to position the ends of the adjacent frame segments in an offset configuration.

29. The retractor of claim 24, wherein the retractor blades are adjustable and each connector is configured to translatably receive a proximal portion of the retractor blade and to reversibly fix the retractor blade position with a locking mechanism incorporated into the connector, wherein the proximal portion of the retractor blade is translatable in the connector until locked by a retractor blade locking mechanism.

30. The retractor of claim 24, wherein the retractor frame is a rounded polygon.

31. The retractor of claim 24, wherein the retractor frame is a rounded quadrilateral.

32. The retractor of claim 24, wherein the outer edge of the frame segment forms the series of notches or teeth.

33. The retractor of claim 24, wherein the arm portions of adjacent frame segments are positioned having the inner edge of one straight arm portion aligned substantially parallel to the outer end of an adjacent frame segment.

34. The retractor of claim 24, wherein the arm portions are 10 to 30 centimeters in length.

35. The retractor of claim 24, wherein the angle between the first straight arm portion and the second straight arm portion is approximately 90 degrees.

36. The retractor of claim 24, wherein the plurality of retractor blades comprise 2, 3, or 4 retractor blades are coupled to the retractor frame.

37. The retractor of claim 24, wherein the plurality of retractor blades comprise 2, 3, or 4 retractor blades are configured to decouple from the retractor frame.

38. The retractor of claim 24, wherein at least one retractor blade is coupled to a connector.

39. The retractor of claim 24, wherein at least one retractor blade is coupled to the frame segment at one of the plurality of arm portions.

40. The retractor of claim 24, wherein at least one retractor blade is configured to be moveable along the curve portion of each frame segment.

41. The retractor of claim 24, wherein the retractor is coupled to a bed frame.

42. The retractor of claim 24, wherein the retractor frame is configured to be attached to patient solely by the plurality of retractor blades after being expanded.

\* \* \* \* \*